(12) United States Patent
Ho et al.

(10) Patent No.: US 11,801,274 B2
(45) Date of Patent: *Oct. 31, 2023

(54) METHOD FOR ALLEVIATING ATOPIC DERMATITIS

(71) Applicant: GLAC BIOTECH CO., LTD., Tainan (TW)

(72) Inventors: Hsieh-Hsun Ho, Tainan (TW); Yi-Wei Kuo, Tainan (TW); Yen-Yu Huang, Tainan (TW); Jia-Hung Lin, Tainan (TW); Ko-Chiang Hsia, Tainan (TW); Ching-Wei Chen, Tainan (TW); Shin-Yu Tsai, Tainan (TW)

(73) Assignee: GLAC BIOTECH CO., LTD., Tainan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/885,189

(22) Filed: Aug. 10, 2022

(65) Prior Publication Data
US 2023/0201278 A1 Jun. 29, 2023

(30) Foreign Application Priority Data
Dec. 29, 2021 (TW) .................................. 110149494

(51) Int. Cl.
*A61K 35/745* (2015.01)
*A61P 29/00* (2006.01)
*A23L 33/135* (2016.01)

(52) U.S. Cl.
CPC .......... *A61K 35/745* (2013.01); *A23L 33/135* (2016.08); *A61P 29/00* (2018.01)

(58) Field of Classification Search
None
See application file for complete search history.

(56) References Cited

U.S. PATENT DOCUMENTS

| 9,011,839 B2 * | 4/2015 | Hsieh | A61P 29/00 424/93.45 |
| 2021/0275612 A1 * | 9/2021 | Liu | A23L 33/135 |
| 2021/0401907 A1 * | 12/2021 | Ho | A61K 8/99 |

OTHER PUBLICATIONS

Rusu et al. Prebiotics and probiotics in atopic dermatitis (Review). Experimental and Therapeutic Medicine, 2019, 18, pp. 926-931.*

* cited by examiner

*Primary Examiner* — Vera Afremova
(74) *Attorney, Agent, or Firm* — Nixon & Vanderhye PC

(57) ABSTRACT

Disclosed herein is a method for alleviating atopic dermatitis using a composition containing at least one lactic acid bacterial strain. The at least one lactic acid bacterial strain is selected from the group consisting of *Lactobacillus salivarius* subsp. *salicinius* AP-32 which is deposited at the China Center for Type Culture Collection (CCTCC) under an accession number CCTCC M 2011127, and *Bifidobacterium animalis* subsp. *lactis* CP-9 which is deposited at the CCTCC under an accession number CCTCC M 2014588.

4 Claims, 6 Drawing Sheets

METHOD FOR ALLEVIATING ATOPIC DERMATITIS

CROSS-REFERENCE TO RELATED APPLICATION

This application claims priority of Taiwanese Invention Patent Application No. 110149494, filed on Dec. 29, 2021.

FIELD

The present disclosure relates to a method for alleviating atopic dermatitis using a composition containing at least one of two lactic acid bacterial strains.

BACKGROUND

Atopic dermatitis (AD) (also known as atopic eczema) is a common and recurrent allergic skin disease. The immunological hallmark of AD is a dysbalance between type 1 T helper (Th1) cells and type 2 T helper (Th2) cells (i.e., Th1/Th2 dysbalance), and increased expression of Th2 cytokines (such as interleukin-13 (IL-13)) is a characteristic finding of human skin with AD. Symptoms of AD include pruritus, skin redness and swelling, desquamation, cracked skin, and crust formation. In infants, the faces are most commonly affected, while in children and adults, the joint flexors of the knees and elbows are most commonly affected. In addition, many AD patients experience symptoms such as allergic rhinitis, asthma, and allergic conjunctivitis.

Currently, drugs used clinically to alleviate AD include oral antihistamines and antibiotics, and topical corticosteroids and immunosuppressive agents. However, these drugs might not be able to achieve the desired therapeutic effect and might also cause severe side effects and drug resistance.

Probiotics are resident normal flora of the intestinal tract, and are believed to play important roles in regulating proper intestinal immunity and digestion by balancing intestinal microflora. These beneficial microorganisms are widely used as live microbial dietary supplements and can help to restore intestinal microflora balance. Many species of lactic acid bacteria (LAB) are conferred with the generally recognized as safe (GRAS) status, and are widely used as probiotics. Common LAB include *Lactobacillus* spp., *Lactococcus* spp., *Pediococcus* spp., *Streptococcus* spp., *Enterococcus* spp., *Bifidobacterium* spp., *Bacillus* spp., *Leuconostoc* spp., etc.

Previous studies have demonstrated that certain strains of LAB are effective in alleviating AD. For example, it has been reported in Isolauri E. et al. (2000), *Clin. Exp. Allergy*, 30:1604-1610 that administration of an extensively hydrolysed whey formula containing *Lactobacillus* strain GG (ATCC 53103) or *Bifidobacterium lactis* BB-12 has been demonstrated to be capable of alleviating allergic inflammation in infants who manifested atopic eczema during exclusive breast-feeding.

In spite of the aforesaid, there is still a need to develop an effective way for alleviating AD.

SUMMARY

Accordingly, the present disclosure provides a method for alleviating atopic dermatitis, which can alleviate at least one of the drawbacks of the prior art, and which includes administering to a subject in need thereof a composition containing at least one lactic acid bacterial strain.

The at least one lactic acid bacterial strain is selected from the group consisting of *Lactobacillus salivarius* subsp. *salicinius* AP-32 which is deposited at the China Center for Type Culture Collection (CCTCC) under an accession number CCTCC M 2011127, and *Bifidobacterium animalis* subsp. *lactis* CP-9 which is deposited at the CCTCC under an accession number CCTCC M 2014588.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

Figure 1:
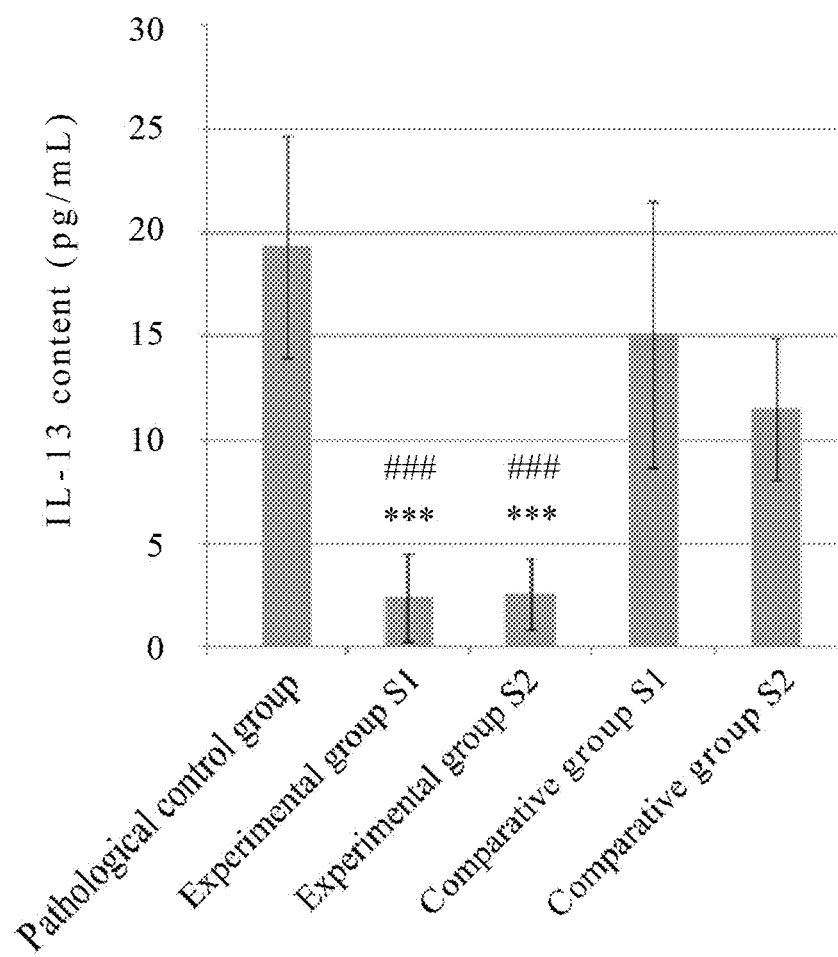
FIG. 1 shows the interleukin-13 (IL-13) contents determined in the pathological control group, experimental groups S1 to S2, and comparative groups S1 to S2 of Example 1, infra, in which the symbol "***" represents $p<0.001$ (compared with the comparative group S1), and the symbol "###" represents $p<0.001$ (compared with the comparative group S2)

For the purpose of this specification, it will be clearly understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art, in Taiwan or any other country.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The present disclosure provides a method for alleviating atopic dermatitis, which includes administering to a subject in need thereof a composition containing at least one lactic acid bacterial strain.

The at least one lactic acid bacterial strain is selected from the group consisting of *Lactobacillus salivarius* subsp. *salicinius* AP-32 which is deposited at the China Center for Type Culture Collection (CCTCC) under an accession number CCTCC M 2011127, and *Bifidobacterium animalis* subsp. *lactis* CP-9 which is deposited at the CCTCC under an accession number CCTCC M 2014588.

As used herein, the term "alleviating" or "alleviation" refers to at least partially reducing, ameliorating, relieving, controlling, treating or eliminating one or more clinical signs of a disease or disorder; and lowering, delaying, stopping or reversing the progression of severity regarding the condition or symptom being treated and preventing or decreasing the likelihood or probability thereof.

As used herein, the term "administering" or "administration" means introducing, providing or delivering the above-mentioned pharmaceutical composition to a subject showing condition(s) or symptom(s) of a disorder by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

According to the present disclosure, the composition may contain *Lactobacillus salivarius* subsp. *salicinius* AP-32 and *Bifidobacterium animalis* subsp. *lactis* CP-9.

In certain embodiments, a number ratio of *Lactobacillus salivarius* subsp. *salicinius* AP-32 to *Bifidobacterium animalis* subsp. *lactis* CP-9 in the composition ranges from 1:0.11 to 1:9. In an exemplary embodiment, the number ratio of *Lactobacillus salivarius* subsp. *salicinius* AP-32 to *Bifidobacterium animalis* subsp. *lactis* CP-9 in the composition is 1:9.

According to the present disclosure, the composition may have a total bacterial concentration ranging from $10^7$ CFU/mL to $10^{12}$ CFU/mL. In certain embodiments, the composition may have a total bacterial concentration ranging from $10^8$ CFU/mL to $10^{10}$ CFU/mL. In an exemplary embodiment, the composition has a total bacterial concentration of $10^9$ CFU/mL.

According to the present disclosure, *Lactobacillus salivarius* subsp. *salicinius* AP-32 and *Bifidobacterium animalis* subsp. *lactis* CP-9 may be live cells or dead cells, concentrated or non-concentrated, a liquid, a paste, a semi-solid, or a solid (e.g., a pellet, a granule, or a powder), and may be heat-inactivated, frozen, dried, or freeze-dried (e.g., may be in freeze-dried form or spray/fluid bed dried form).

According to the present disclosure, the composition may be formulated as a food product using a standard technique well known to one of ordinary skill in the art. For example, the composition may be directly added to an edible material or may be used to prepare an intermediate composition (e.g., a food additive or a premix) suitable to be subsequently added to the edible material.

As used herein, the term "food product" refers to any article or substance that can be ingested by a subject into the body thereof. Examples of the food product may include, but are not limited to, milk powders, fermented milk, yogurt, butter, beverages (e.g., tea, coffee, etc.), functional beverages, a flour product, baked foods, confectionery, candies, fermented foods, animal feeds, health foods, infant foods, and dietary supplements.

According to the present disclosure, the composition may be prepared in the form of a pharmaceutical composition. The pharmaceutical composition may be formulated into a dosage form suitable for oral or topical administration using technology well known to those skilled in the art.

According to the present disclosure, the dosage form suitable for oral administration includes, but is not limited to, sterile powders, tablets, troches, lozenges, pellets, capsules, dispersible powders or granules, solutions, suspensions, emulsions, syrup, elixir, slurry, and the like.

According to the present disclosure, the pharmaceutical composition may be formulated into an external preparation suitable for topical application to the skin using technology well known to those skilled in the art. The external preparation includes, but is not limited to, emulsions, gels, ointments, creams, patches, liniments, powder, aerosols, sprays, lotions, serums, pastes, foams, drops, suspensions, salves, and bandages.

According to the present disclosure, the external preparation is prepared by admixing the pharmaceutical composition with a base that is well known and commonly used in the art.

According to the present disclosure, the base may include one or more of the following additives: water, alcohols, glycols, hydrocarbons (such as petroleum jelly and white petrolatum), waxes (such as paraffin and yellow wax), preserving agents, antioxidants, surfactants, absorption enhancers, stabilizing agents, gelling agents (such as Carbopol®941, microcrystalline cellulose and carboxymethylcellulose), active agents, humectants, odor absorbers, fragrances, pH-adjusting agents, chelating agents, emulsifiers, occlusive agents, emollients, thickeners, solubilizing agents, penetration enhancers, anti-irritants, colorants, propellants, etc. The choice and amount of the aforesaid additives are within the expertise and the routine skills of those skilled in the art.

According to the present disclosure, the pharmaceutical composition may further include a pharmaceutically acceptable carrier widely employed in the art of drug-manufacturing. For instance, the pharmaceutically acceptable carrier may include one or more of the following agents: solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and the like. The choice and amount of the aforesaid agents are within the expertise and routine skills of those skilled in the art.

According to the present disclosure, the pharmaceutical composition may further include an additional component for maintaining or improving skin health. The additional component includes, but is not limited to, an anti-inflammatory agent, an immunosuppressive agent, antihistamines, an antiviral agent, a wound-healing agent, antipruritics, an anti-dry skin agent, a humectant, and a skin nutrient.

The dose and frequency of administration of the pharmaceutical composition may vary depending on the following factors: the severity of the illness or disorder to be treated, routes of administration, and age, physical condition and response of the subject to be treated. In general, the pharmaceutical composition may be administered in a single dose or in several doses.

The disclosure will be further described by way of the following examples. However, it should be understood that the following examples are solely intended for the purpose of illustration and should not be construed as limiting the disclosure in practice.

EXAMPLES

General Experimental Materials

1. Lactic Acid Bacterial (LAB) Strains

*Lactobacillus salivarius* subsp. *salicinius* AP-32 (which is disclosed in TW 1384990 B and CN 102835666 B) and *Bifidobacterium animalis* subsp. *lactis* CP-9 (which is disclosed in TW 1572713 B and CN 105985918 B) have been deposited at the Bioresource Collection and Research Center (BCRC) of the Food Industry Research and Development Institute (FIRDI) (No. 331, Shih-Pin Rd., Hsinchu City 300, Taiwan), and have also been deposited at the China Center for Type Culture Collection (CCTCC) of Wuhan University, the College of Life Sciences (No. 299, Bayi Rd., Wuchang District, Wuhan City, Hubei Province, 430072, China) in accordance with the Budapest Treaty.

The relevant information regarding each of the LAB strains (including accession number and date of deposit) is listed in Table 1 below.

TABLE 1

| LAB strains | Accession number | Date of deposit |
|---|---|---|
| *Lactobacillus salivarius* subsp. *salicinius* AP-32 | BCRC 910437<br>CCTCC M 2011127 | Jul. 30, 2009<br>Apr. 10, 2011 |
| *Bifidobacterium animalis* subsp. *lactis* CP-9 | BCRC 910645<br>CCTCC M 2014588 | Aug. 21, 2014<br>Nov. 24, 2014 |

In addition, two LAB strains were used as comparative strains, including *Bifidobacterium animalis* subsp. *lactis* BB-12 (DSM 15954) and *Lactobacillus rhamnosus* GG (LGG) (ATCC 53103) which were purchased from Chr. Hansen A/S. Denmark.

2. Preparation of Bacterial Suspension of LAB Strain

A respective one of the four LAB strains described in section 1 of "General Experimental Materials" was inoculated in a MRS (De Man, Rogosa and Sharpe) broth (Cat. No. 288130, BD Difco) supplemented with 0.05% (w/w) cysteine, followed by cultivation in an incubator (37° C., 5% $CO_2$) for 24 hours to obtain a inoculum. Thereafter, the inoculum was inoculated in an amount of 2% (v/v) into a MRS broth, followed by cultivation in an incubator (37° C., 5% $CO_2$) for 24 hours.

After centrifugation at 3,000 rpm for 10 minutes, the resultant cell pellet was collected, and was then suspended in an appropriate amount of a MRS broth, thereby obtaining a bacterial suspension having a bacterial concentration of $1 \times 10^9$ CFU/mL, which was determined using a plate counting medium. The bacterial suspensions of the aforesaid LAB strains were used in the following experiments.

3. Preparation of Human Peripheral Blood Mononuclear Cells (Human PBMCs)

Blood samples were collected from 10 human volunteers with atopic dermatitis (AD) (which were recruited from Kaohsiung Chang Gung Memorial Hospital, Taiwan), and an acid citrate dextrose (ACD) solution was used as an anticoagulant. The blood samples were subjected to density gradient centrifugation (720 g, minutes) at 4° C. with Ficoll-Paque™ PLUS. Thereafter, the lymphocyte layer was harvested, followed by adding a red blood cell (RBC) lysis buffer. After centrifugation at 3,000 rpm and 4° C. for 10 minutes, the red blood cells were removed, so as to obtain human PBMCs, and the cell concentration was adjusted to $4 \times 10^6$ cells/mL using an RPMI 1640 medium (Gibco) containing 10% fetal bovine serum (FBS).

General Procedures:

1. Statistical Analysis

All the experiments described below were performed in triplicates. The experimental data of all the test groups are expressed as mean±standard error of the mean (SEM), and were analyzed using Student's t-test, so as to evaluate the differences between the groups. Statistical significance is indicated by $p<0.05$.

Example 1. Evaluation for the Effect of Bacterial Suspension of LAB Strain According to this Disclosure on Alleviation of AD Methods:

The human PBMCs prepared in section 3 of "General Experimental Materials" were divided into 10 groups, including one pathological control group, two comparative groups (i.e., comparative groups 51 and S2), and seven experimental groups (i.e., experimental groups S1 to S2 and experimental groups M1 to M5). Each group of the human PBMCs was incubated in a respective well of a 96-well culture plate containing 0.12 mL of an RPMI 1640 medium (supplemented with 10% FBS and 1% penicillin-streptomycin (PS)) at $4 \times 10^5$ cells/well, followed by cultivation in an incubator (37° C., 5% $CO_2$) for 24 hours.

Next, medium change was performed by adding a fresh RPMI 1640 medium into the 96-well culture plate. Afterwards, each of the cell cultures of the experimental groups S1 to S2 and the comparative groups S1 to S2 was treated with a suitable amount of the respective bacterial suspension of LAB prepared in section 2 of "General Experimental Materials" as shown in Table 2 below. The cell culture of the pathological control group received no treatment.

TABLE 2

| Group | Bacterial suspension of LAB (bacterial number: $4 \times 10^6$ CFU) |
|---|---|
| Pathological control group | — |
| Experimental group S1 | Bacterial suspension of *Lactobacillus salivarius* subsp. *salicinius* AP-32 |
| Experimental group S2 | Bacterial suspension of *Bifidobacterium animalis* subsp. *lactis* CP-9 |
| Comparative group S1 | Bacterial suspension of *Lactobacillus rhamnosus* GG |
| Comparative group S2 | Bacterial suspension of *Bifidobacterium animalis* subsp. *lactis* BB-12 |

In addition, the bacterial suspensions of *Lactobacillus salivarius* subsp. *salicinius* AP-32 and *Bifidobacterium animalis* subsp. *lactis* CP-9 were mixed in different number ratios to obtain 5 suspension mixtures (i.e., suspension mixtures 1 to 5). Each of the cell cultures of the experimental groups M1 to M5 was treated with a suitable amount of the respective suspension mixture as shown in Table 3 below.

TABLE 3

| Group | Suspension mixture | Number ratio of *Lactobacillus salivarius* subsp. *salicinius* AP-32 to *Bifidobacterium animalis* subsp. *lactis* CP-9 |
|---|---|---|
| Experimental | 1 | 1:0.05 |

TABLE 3-continued

| Group | Suspension mixture | Number ratio of Lactobacillus salivarius subsp. salicinius AP-32 to Bifidobacterium animalis subsp. lactis CP-9 |
|---|---|---|
| Experimental group M1 | 1 | |
| Experimental group M2 | 2 | 1:0.11 |
| Experimental group M3 | 3 | 1:1 |
| Experimental group M4 | 4 | 1:9 |
| Experimental group M5 | 5 | 1:19 |

Each group was cultivated in an incubator (37° C., 5% $CO_2$) for 48 hours. After centrifugation at 3,000 rpm for 10 minutes, the resultant supernatant was collected, and was then subjected to determination of interleukin-13 (IL-13), IL-10, and interferon-γ (IFN-γ) contents using an IL-13 ELISA kit (Cat. No. BMS231-3, ThermoFisher), an IL-10 ELISA kit (Cat. No. BMS215-2, ThermoFisher), and an IFN-γ ELISA kit (Cat. No. KHC4021, ThermoFisher), respectively, in accordance with the manufacturer's instructions.

The data thus obtained were analyzed according to the method described in section 1 of "General Procedures".

Figure 2:
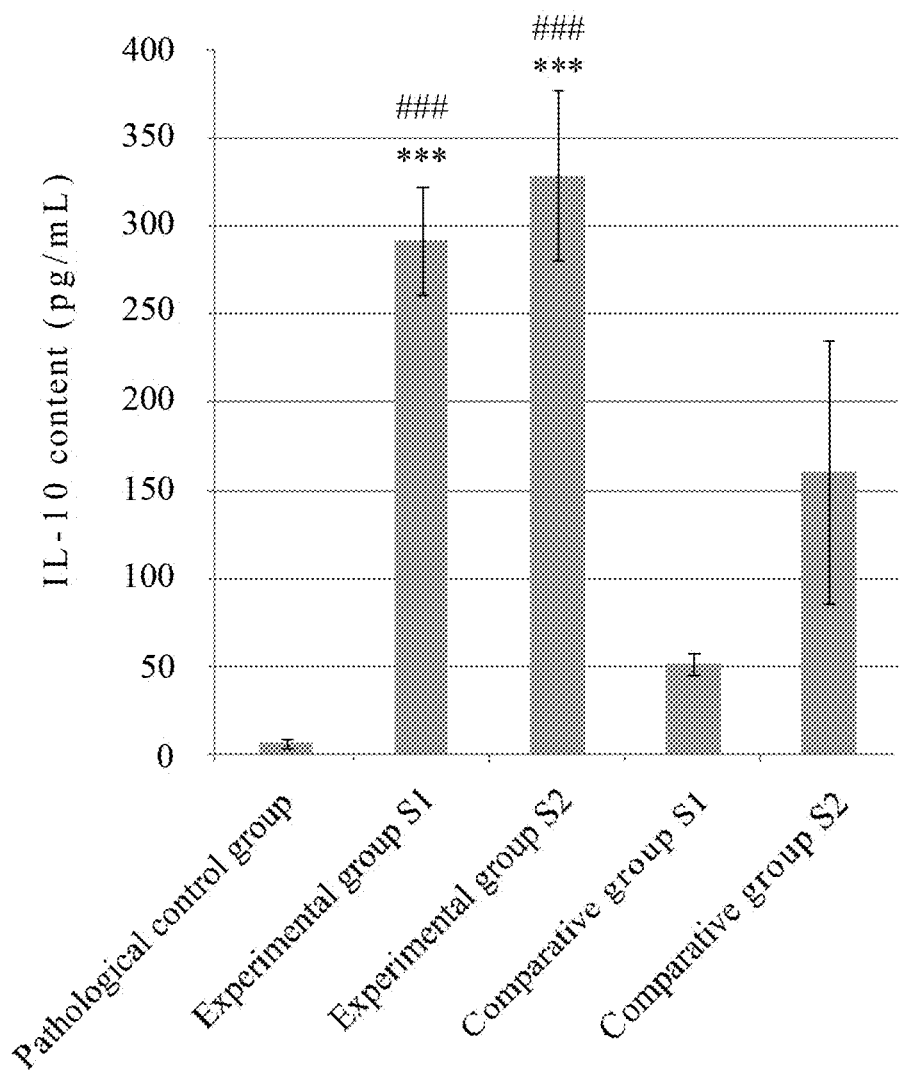
FIG. 2 shows the IL-10 contents determined in the pathological control group, experimental groups S1 to S2, and comparative groups S1 to S2 of Example 1, infra, in which the symbol "***" represents $p<0.001$ (compared with the comparative group S1), and the symbol "###" represents $p<0.001$ (compared with the comparative group S2)
Figure 3:
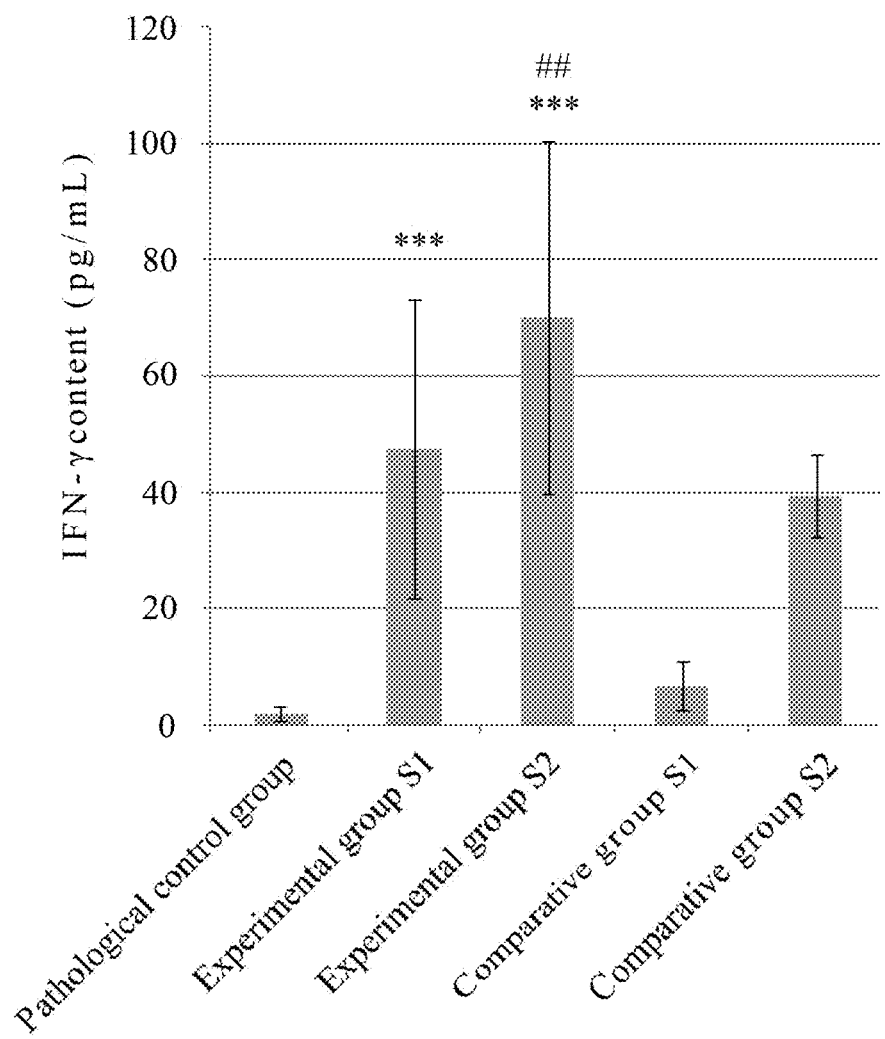
FIG. 3 shows the interferon-γ (IFN-γ) contents determined in the pathological control group, experimental groups S1 to S2, and comparative groups S1 to S2 of Example 1, infra, in which the symbol "***" represents $p<0.001$ (compared with the comparative group S1), and the symbol "##" represents $p<0.01$ (compared with the comparative group S2)

Results:

Referring to FIGS. 1 to 3, the IL-13 contents determined in the experimental groups S1 and S2 were significantly lower than those determined in the comparative groups S1 to S2 and the pathological control group, and the contents of IL-10 and IFN-γ determined in the experimental groups S1 and S2 were significantly higher than those determined in the comparative groups S1 to S2 and the pathological control group.

These results indicate that the bacterial suspension of any one of Lactobacillus salivarius subsp. salicinius AP-32 and Bifidobacterium animalis subsp. lactis CP-9 is capable of effectively inhibiting the secretion of IL-13 from Th2 cells and inducing the secretion of IL-10 and IFN-γ from Th1 cells, and hence can exhibit anti-allergic activity.

Figure 4:
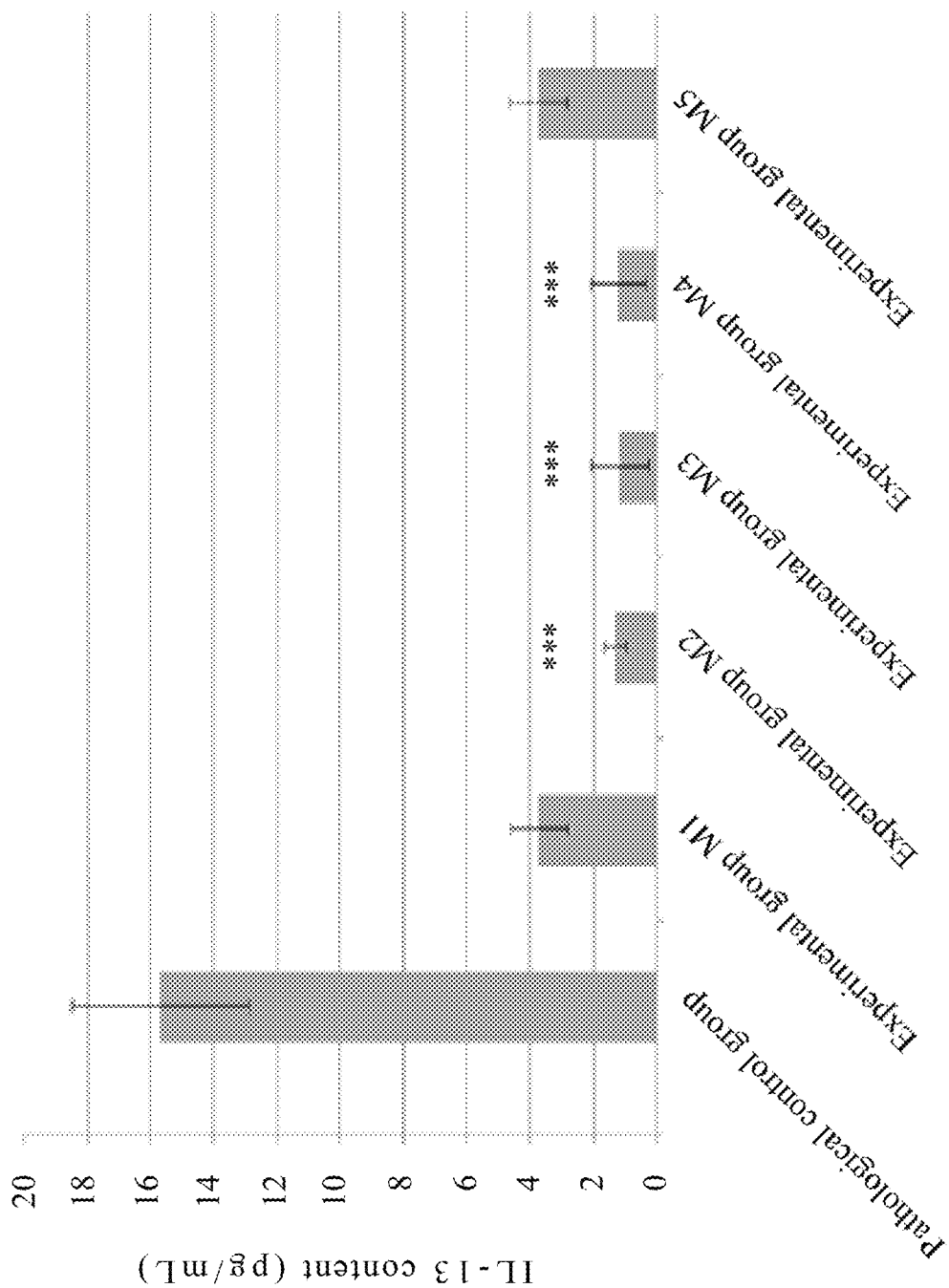
FIG. 4 shows the IL-13 contents determined in the pathological control group and experimental groups M1 to M5 of Example 1, infra, in which the symbol "***" represents $p<0.001$ (compared with the pathological control group)
Figure 5:
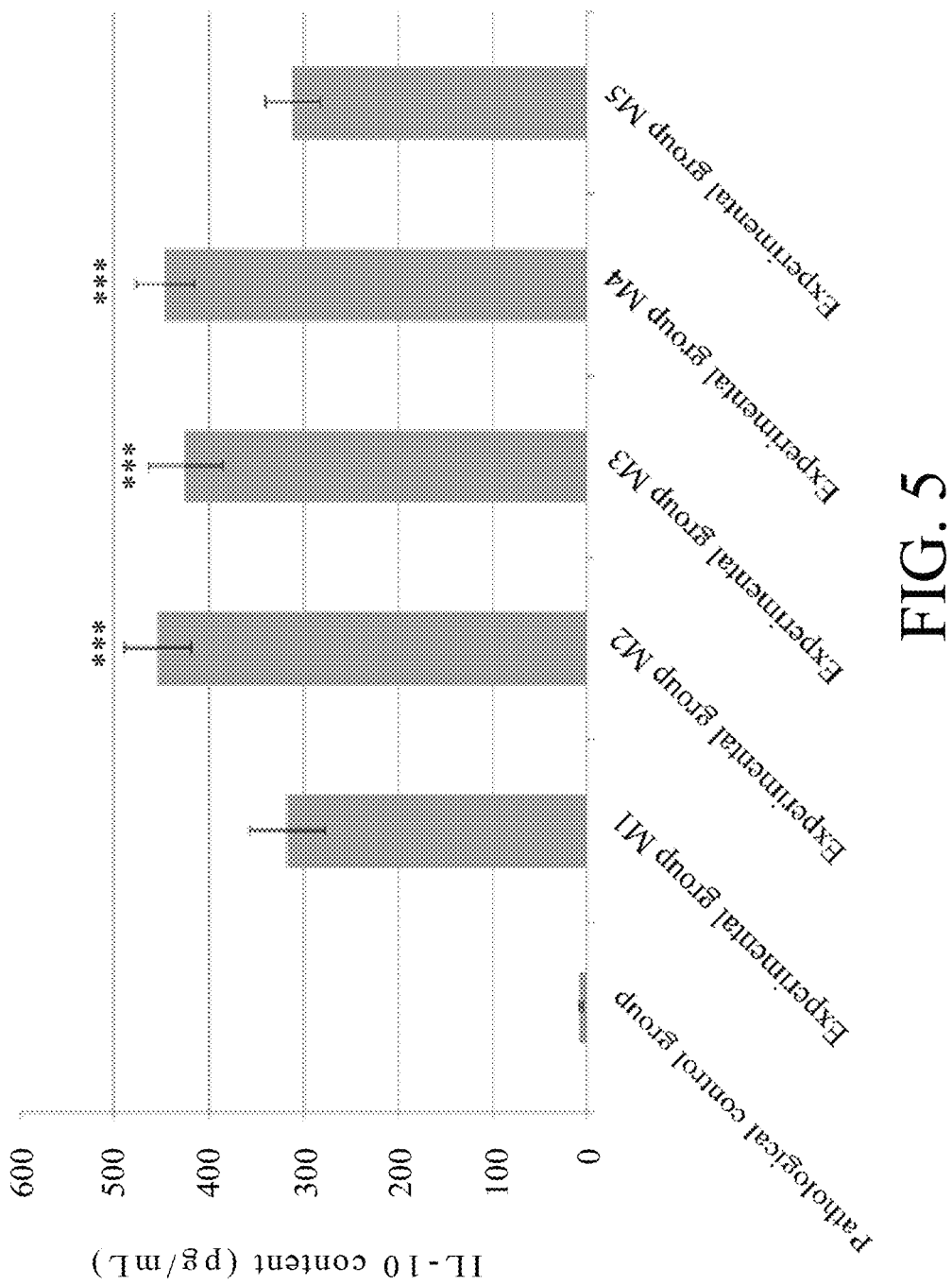
FIG. 5 shows the IL-10 contents determined in the pathological control group and experimental groups M1 to M5 of Example 1, infra, in which the symbol "*" represents $p<0.001$ (compared with the pathological control group)
Figure 6:
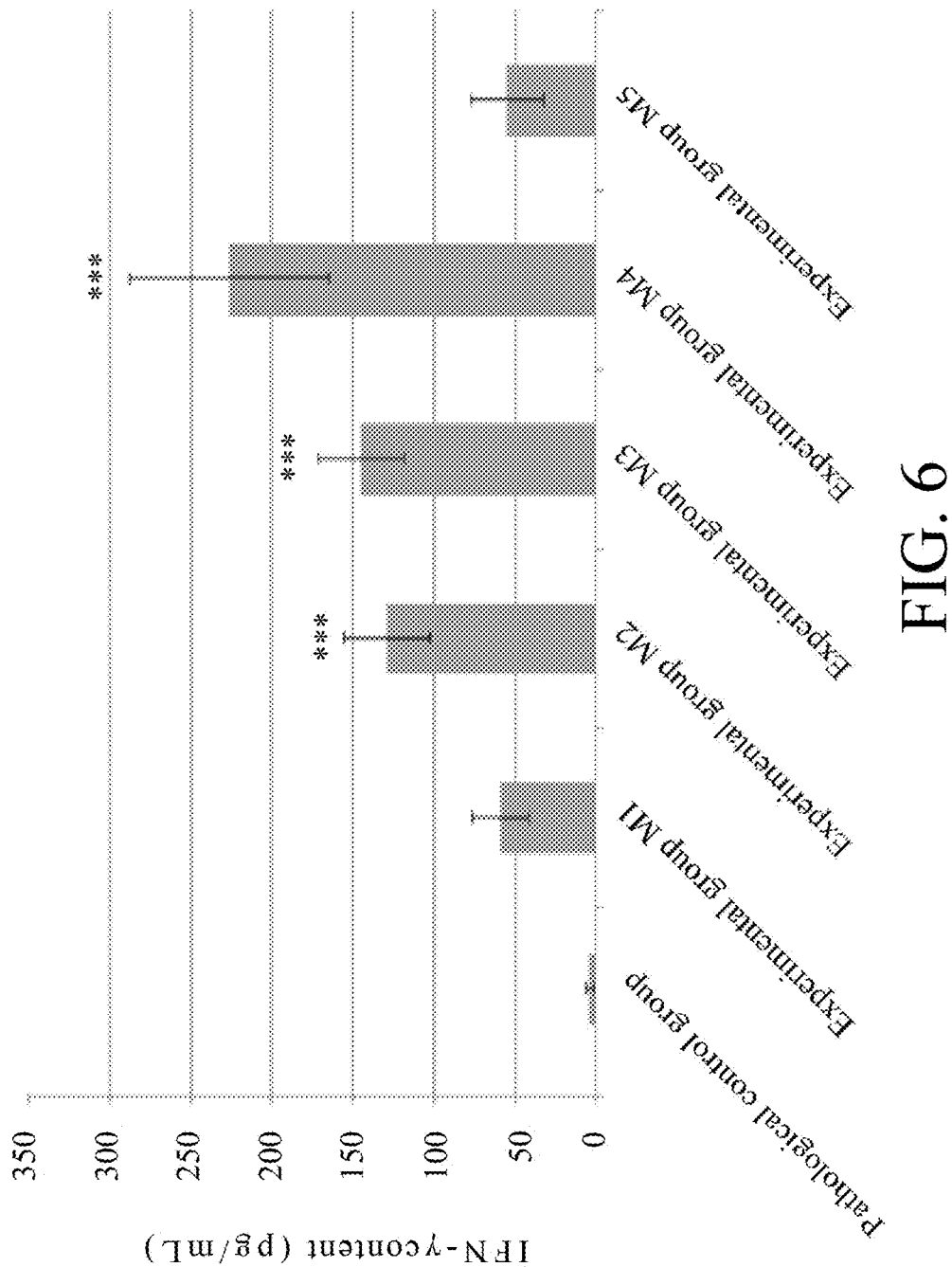
FIG. 6 shows the IFN-γ contents determined in the pathological control group and experimental groups M1 to M5 of Example 1, infra, in which the symbol "*" represents $p<0.001$ (compared with the pathological control group).

In addition, referring to FIGS. 4 to 6, the IL-13 contents determined in the experimental groups M1 to M5 were significantly lower than that determined in the pathological control group, and the contents of IL-10 and IFN-γ determined in the experimental groups M1 to M5 were significantly higher than those determined in the pathological control group.

These results indicate that the bacterial suspension of Lactobacillus salivarius subsp. salicinius AP-32 and the bacterial suspension of Bifidobacterium animalis subsp. lactis CP-9, when mixed in a specified number ratio, exhibit a synergistic effect on anti-allergic activity.

Summarizing the above test results, it is clear that each of the Lactobacillus salivarius subsp. salicinius AP-32 and Bifidobacterium animalis subsp. lactis CP-9 is capable of effectively alleviating atopic dermatitis, and when used in combination, can synergistically exhibit a further improved efficacy.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for alleviating atopic dermatitis, comprising administering to a subject in need thereof a composition containing Lactobacillus salivarius subsp. salicinius AP-32 which is deposited at the China Center for Type Culture Collection (CCTCC) under an accession number CCTCC M 2011127, and Bifidobacterium animalis subsp. lactis CP-9 which is deposited at the CCTCC under an accession number CCTCC M 2014588, wherein a number ratio of Lactobacillus salivarius subsp. salicinius AP-32 to Bifidobacterium animalis subsp. lactis CP-9 ranges from 1:0.11 to 1:9.

2. The method as claimed in claim 1, wherein the composition is formulated as a food product.

3. The method as claimed in claim 1, wherein the composition is formulated as a pharmaceutical composition.

4. The method as claimed in claim 3, wherein the pharmaceutical composition is in a dosage form selected from the group consisting of an oral dosage form and a topical dosage form.

\* \* \* \* \*